(12) United States Patent
Carriazo

(10) Patent No.: US 11,759,312 B2
(45) Date of Patent: Sep. 19, 2023

(54) HOLDING APPARATUS FOR HOLDING AN OPTICAL IMPLANT AT A WALL REGION IN AN EYE INTERIOR OF AN EYE, AND OPTICAL APPARATUS COMPRISING A HOLDING APPARATUS AND AN OPTICAL IMPLANT

(71) Applicant: Cesar C. Carriazo, Baranquilla (CO)

(72) Inventor: Cesar C. Carriazo, Baranquilla (CO)

( * ) Notice: Subject to any disclaimer, the term of this patent is extended or adjusted under 35 U.S.C. 154(b) by 56 days.

(21) Appl. No.: 17/254,620

(22) PCT Filed: Jun. 6, 2019

(86) PCT No.: PCT/IB2019/054730
§ 371 (c)(1),
(2) Date: Mar. 15, 2021

(87) PCT Pub. No.: WO2019/243937
PCT Pub. Date: Dec. 26, 2019

(65) Prior Publication Data
US 2021/0196449 A1   Jul. 1, 2021

(30) Foreign Application Priority Data
Jun. 19, 2018   (DE) .................... 20 2018 103 444.8

(51) Int. Cl.
*A61F 2/16*   (2006.01)
(52) U.S. Cl.
CPC .............. *A61F 2/1648* (2013.01); *A61F 2/16* (2013.01); *A61F 2002/1686* (2013.01); *A61F 2002/16902* (2015.04); *A61F 2220/0016* (2013.01)

(58) Field of Classification Search
CPC .. A61F 2002/16902; A61F 2002/16903; A61F 2/1648; A61F 2/1605; A61F 2/1608
See application file for complete search history.

(56) References Cited

U.S. PATENT DOCUMENTS

| 2005/0090896 A1* | 4/2005 | Ben Nun ............... A61F 2/1613 |
| | | 623/6.43 |
| 2008/0004699 A1 | 1/2008 | Ben Nun |
| 2015/0150676 A1* | 6/2015 | Nun ....................... A61F 2/1635 |
| | | 623/6.37 |

FOREIGN PATENT DOCUMENTS

| DE | 199 25 636 B4 | 7/2007 |
| WO | 9810717 A1 | 3/1998 |
| WO | 2014137306 A1 | 9/2014 |
| WO | 2016182520 A1 | 11/2016 |
| WO | 2017116357 A1 | 7/2017 |
| WO | 2017183359 A1 | 10/2017 |

* cited by examiner

*Primary Examiner* — William H Matthews
(74) *Attorney, Agent, or Firm* — Hinckley, Allen & Snyder, LLP; David R. Josephs

(57) ABSTRACT

The present invention relates to a holding device for holding an optical implant on a wall area in an eye interior of an eye, comprising at least one retaining component, by which a contact pressure can be exerted on the wall area and thereby the at least one retaining component can be supported on the wall area. Therein, the at least one retaining component has at least one protrusion region, from which at least one protrusion element extends away, which is designed to, when the contact pressure is exerted, penetrate at least regionally into a wall area tissue of the wall area and/or to exert punctiform pressure on the wall area. The invention further relates to an optical device.

11 Claims, 5 Drawing Sheets

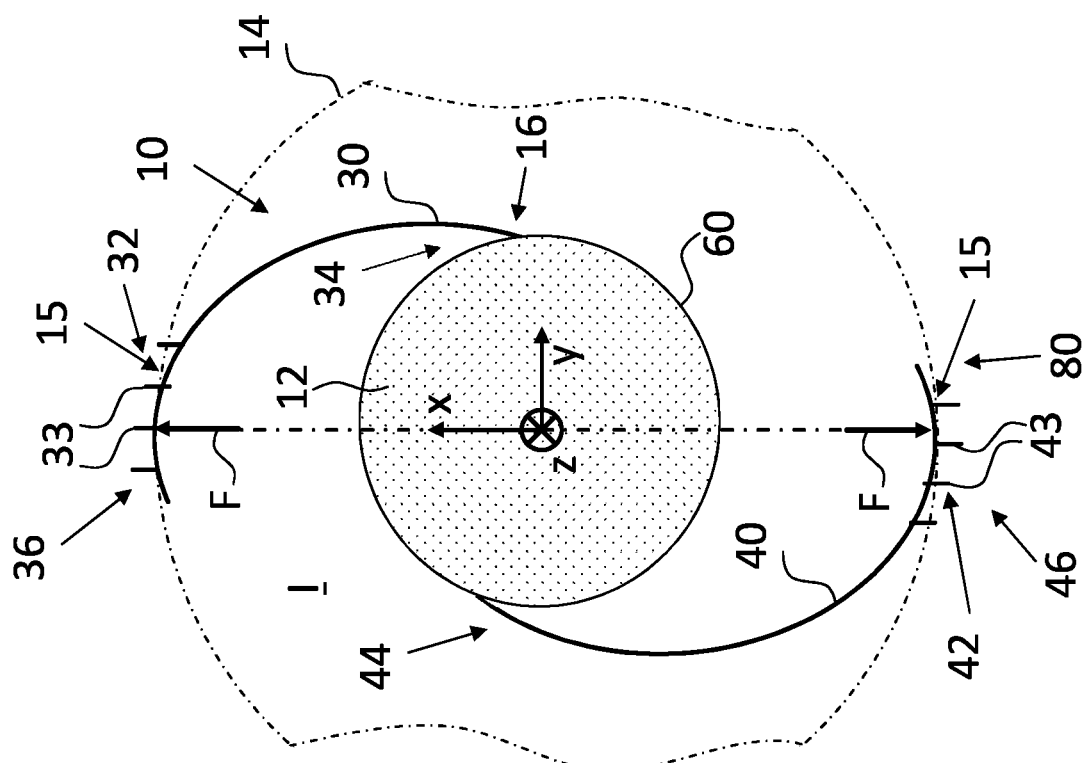
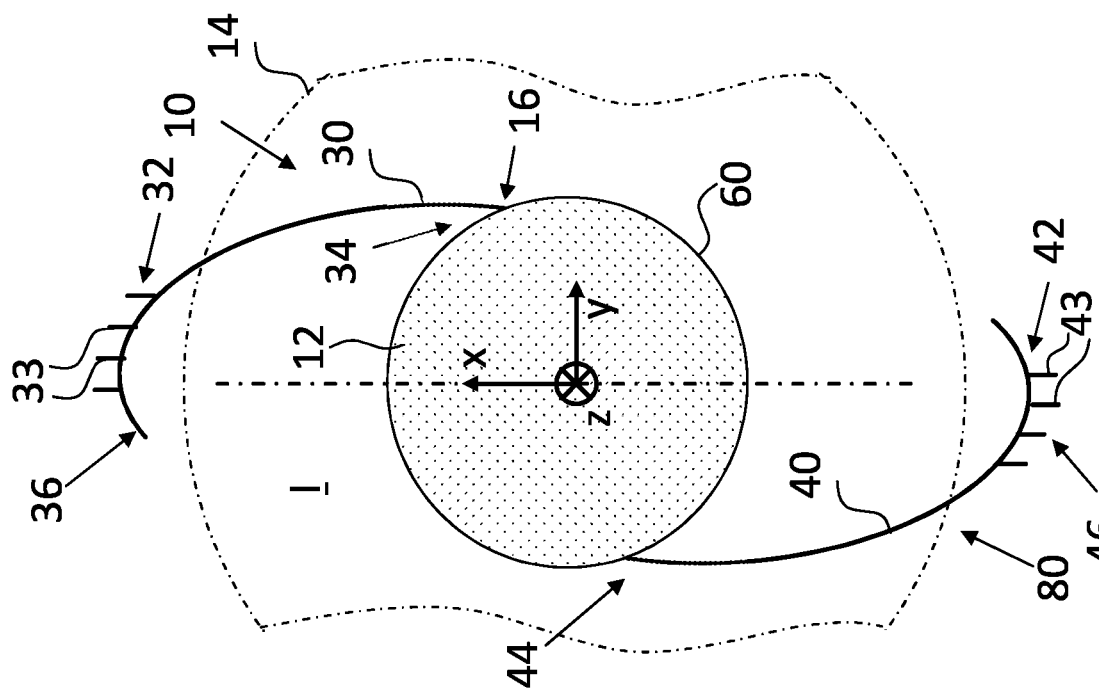

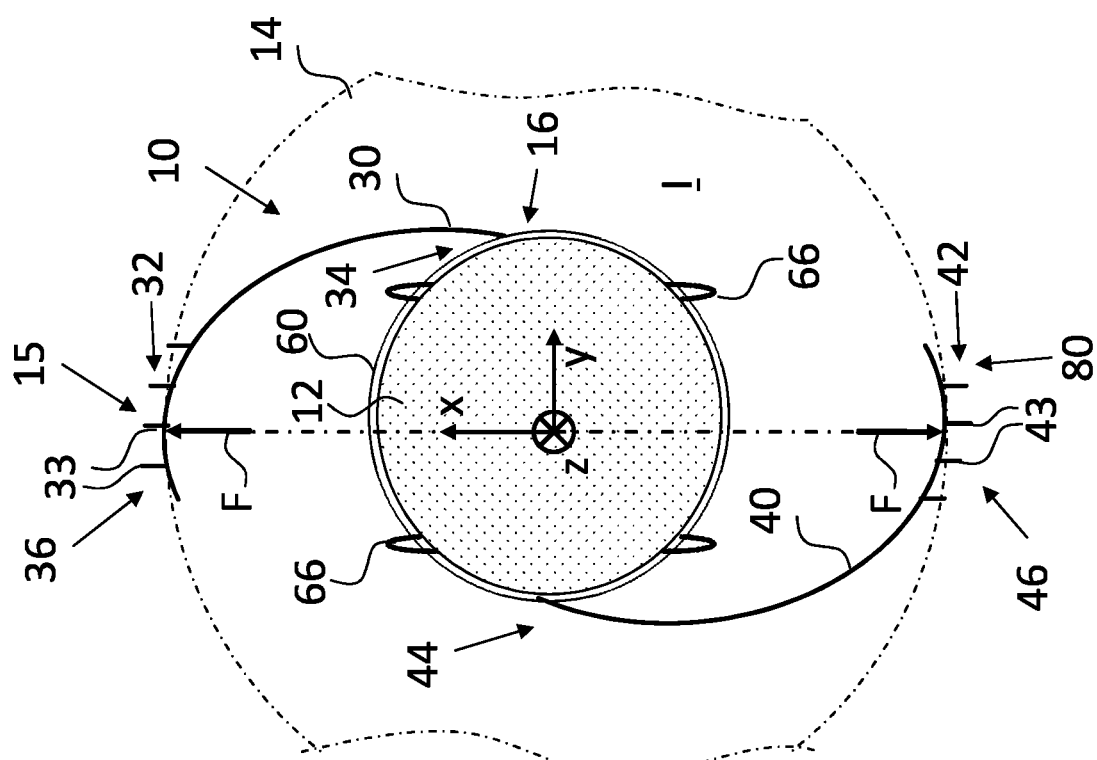
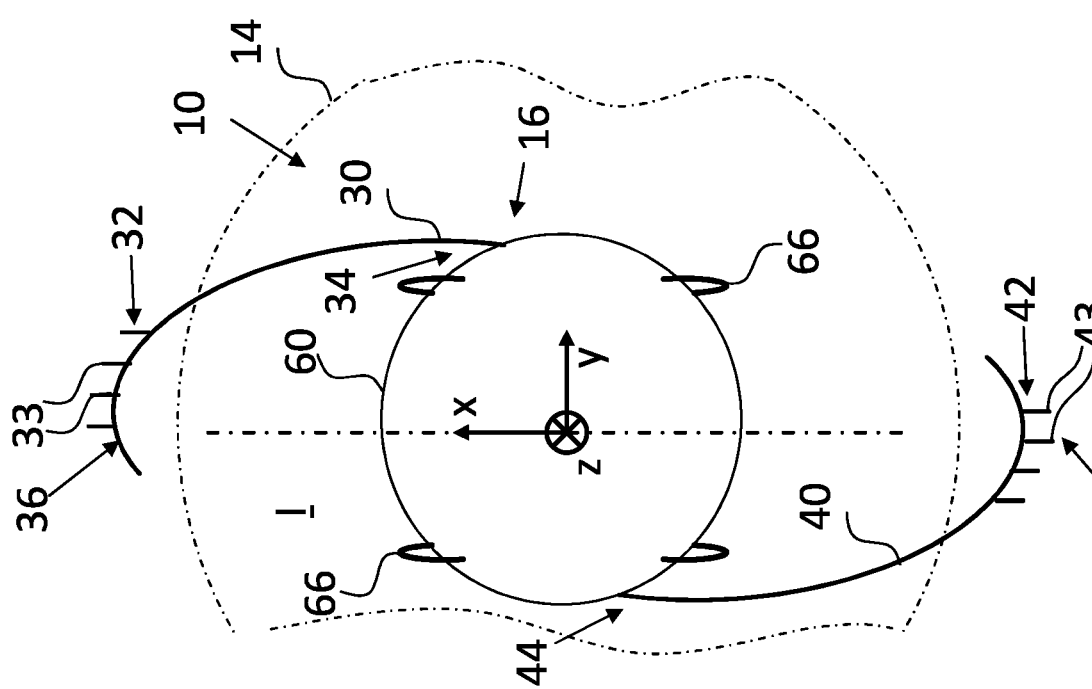
Fig. 2a
Fig. 2b

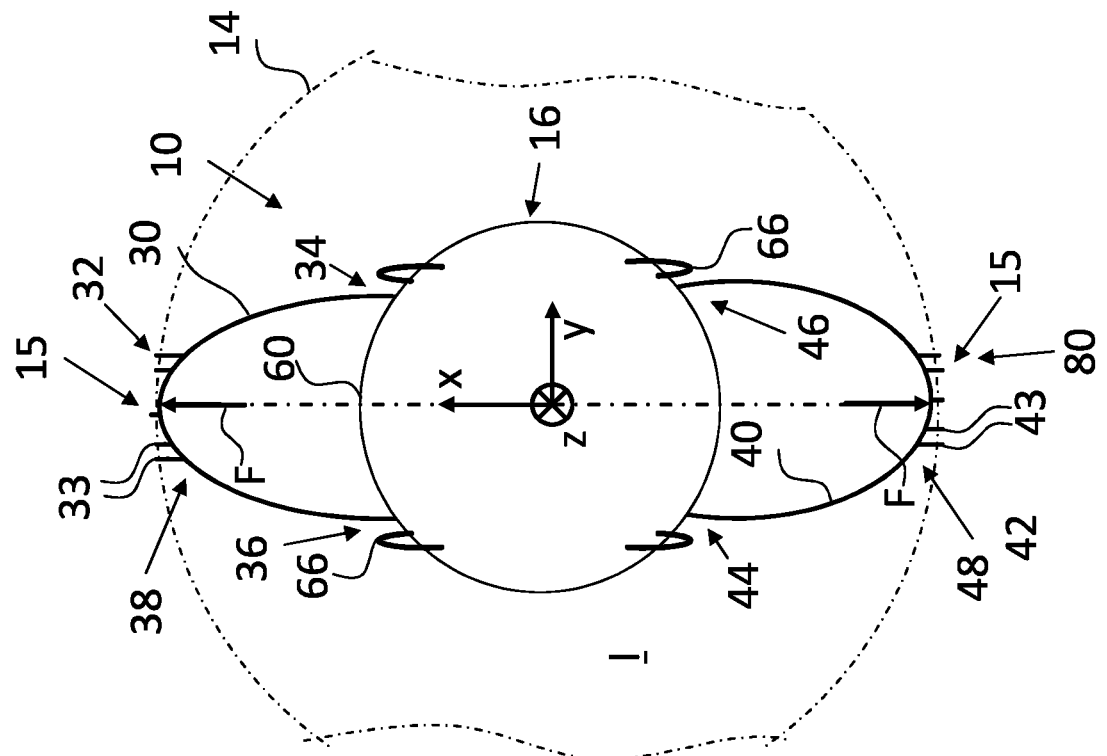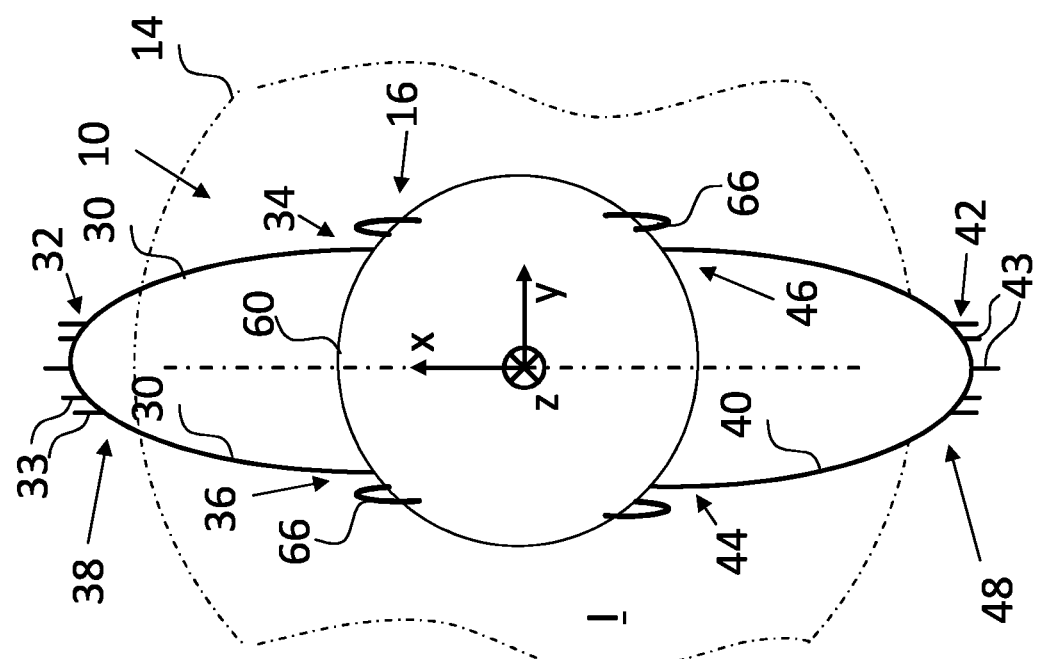

US 11,759,312 B2

HOLDING APPARATUS FOR HOLDING AN OPTICAL IMPLANT AT A WALL REGION IN AN EYE INTERIOR OF AN EYE, AND OPTICAL APPARATUS COMPRISING A HOLDING APPARATUS AND AN OPTICAL IMPLANT

BACKGROUND OF THE INVENTION

The invention relates to a holding device for holding an optical implant to a wall area in an eye interior of an eye. Another aspect of the invention relates to an optical device having such a holding device and having an optical implant held on the holding device.

Various types and models of optical devices are known from the prior art, which can be designed as intraocular eye lenses, also called intraocular lenses. The intraocular lens is usually sutured in a capsular bag or in a sulcus (scleral sulcus, sulcus sclerae) in the course of an implantation, especially if the intraocular lens cannot be supported sufficiently securely in the eye, for example at the capsular bag. A main cause of damage to the capsular bag is a so-called capsular rupture as a result of a surgical complication during cataract surgery, but diseases or situations are also known to cause detachment of the capsular bag or subluxations. Only examples are detachments or subluxations due to Marfan syndrome or trauma. In general, intraocular lenses consist of an optical system which is connected to flexible haptic elements so that not only a minimally invasive insertion, e.g. into the capsular bag, is rendered possible, but also a sufficiently secure centering.

WO 98/10717 A1 describes an artificial intraocular eye lens with a deformable optical zone region for implantation during cataract surgery, comprising a lens and four angular elastic haptic elements connected thereto, which are peripherally separated from each other, all arranged in one direction of rotation in such a way that in a folded state the haptic elements come to lie in the implantation region without additional manipulations. The haptic elements have notches or holes suitable for allowing suture fixation, for example in the sulcus ciliaris.

DE 199 25 636 B4 describes an intraocular lens for implantation in the anterior chamber of the eye, consisting of a centrally arranged lens body which is provided at its periphery with haptic elements for fixation to the front of the iris, the haptic elements each having two pincer-like arms extending outwards from the periphery of the lens body, between the ends of which a gap is formed in which the iris can be clamped.

SUMMARY OF THE INVENTION

It is the object of the present invention to provide a holding device and an optical device of the type mentioned above, which can be fixed in an eye interior with particularly little effort.

This object is solved by a holding device and by an optical device of the present invention. Advantageous embodiments are described in detail below.

A first aspect of the invention relates to a holding device for holding an optical implant on a wall area in an eye interior of an eye, comprising at least one retaining component by which a contact pressure can be exerted on the wall area and thereby the at least one retaining component can be supported on the wall area. The optical implant can be designed, for example, as an intraocular lens, by which visual disturbances can be compensated with little effort. Furthermore, the optical implant can be designed as a prosthesis, i.e. as an artificial replica of at least one portion of the eye, so that cosmetic correction is rendered possible by using the optical implant. The wall area can directly delimit the interior of the eye, at least in certain areas. The wall area can be, for example, a sulcus (also called scleral sulcus) or a capsular bag of the eye. Compared to other eye areas, the sulcus and capsular bag are particularly stable and resilient and thus particularly suitable for supporting the at least one retaining component while exerting contact pressure on it. The at least one retaining component may be configured for direct support on the wall area. In the case of direct support, any intermediate elements between the retaining component and the wall area can be dispensed with in an advantageous manner, thus enabling the holding device to be fixed in the interior of the eye with particularly little effort.

According to the invention, the at least one retaining component has at least one protrusion region, from which at least one protrusion element extends away, which is designed to, when the contact pressure is exerted, penetrate at least in certain areas into a wall area tissue of the wall area and/or to exert punctiform pressure on the wall area. This is advantageous, as it enables the holding device to be fixed to the wall area in the interior of the eye with particularly little effort. The protrusion element makes it possible, for example, to dispense with suturing, i.e. suture fixation of the holding device, which makes it possible to fix the holding device in the interior of the eye with particularly little effort. The regionally penetration into the wall area tissue or the punctual exertion of pressure enables a simple, low-effort fixation of the holding device. The regionally penetration therein is advantageous because it allows a plastic deformation of the wall area and a form fit to be formed between the retaining component and the wall area, which makes it possible to fix the holding device particularly reliably and to secure it against rotation (anti-rotation) in the interior of the eye.

In the context of the present disclosure, the punctual exertion of pressure can be understood as an exertion of at least one point load on the wall area. This is advantageous, since a particularly large friction between the holding device and the wall area can be achieved by the point load. As a result, a punctiform pressing-in of the wall area can be effected and thus a particularly advantageous positional securing of the retaining component can be achieved.

In the context of the present disclosure, the punctual exertion of pressure can also be understood as an exertion of at least one line load on the wall area. This is advantageous, since the application of the line load enables a linear pressure distribution on the wall area, whereby a particularly advantageous positional securing of the retaining component can also be achieved.

The at least one protrusion element can preferably be designed as a tip or as a hook. This enables easy penetration into the wall area tissue of the wall area and additionally or alternatively effective, punctual exertion of pressure on the wall area.

Alternatively, the at least one protrusion element can also preferably be designed as a strut element. The strut element can have a triangular cross-section in a plane perpendicular to its main extension direction. This also enables easy penetration into the wall area tissue of the wall area and, additionally or alternatively, effective, punctiform exertion of pressure on the wall area.

The holding device may be configured to be generally foldable to facilitate insertion of the holding device into the interior of the eye. After insertion into the eye interior, the holding device may be unfolded to secure the holding device within the eye interior.

The invention is based on the understanding that, although minimal injury to the wall area tissue may occur with the regionally penetration of the at least one protrusion element into the wall area tissue, such injury can be tolerated to reliably secure the holding device with minimal effort. Furthermore, it is recognized that even by exerting pressure punctually by the at least one protrusion element, a lower contact pressure force compared to systems known from the prior art (with intraocular lenses) can be sufficient to achieve reliable fixation without the need for suture fixation. This is due to the fact that the punctual exertion of pressure can achieve a punctual elastic indentation of the wall area, whereby—in contrast to a flat contact between the holding device and the wall area—a particularly large frictional force or holding force can be achieved locally between the wall area and the protrusion element.

In an advantageous further development of the invention, the at least one retaining component comprises at least two haptic elements by which the contact pressure force can be exerted on the wall area, the at least one protrusion region being arranged on at least one haptic element of the at least two haptic elements. This is advantageous because a particularly simple centering of the retaining component is facilitated via the at least two haptic elements. For this purpose, the at least two haptic elements can be arranged opposite each other, for example in a longitudinal extension direction of the holding device, whereby a simple, centered holding of the holding device in the eye interior is facilitated. The at least one protrusion region may be arranged at a distal end of the respective haptic element.

The at least one retaining component can particularly preferably comprise exactly two haptic elements. In contrast to systems known from the prior art with, for example, four haptic elements, this allows tensions on the eye to be kept particularly low when fixing the retaining component, thus allowing for avoiding unnecessary strain on the eye. If the retaining component comprises exactly two haptic elements, these two haptic elements can be aligned point-symmetrically with respect to each other in a particularly preferred manner. A particularly uniform, low-stress and thus tissue-conserving load on the wall area can be achieved by a point-symmetrical alignment. In particular, the point-symmetrical alignment can keep any tissue strains at the wall area between the two haptic elements particularly low.

It is also advantageous if all the haptic elements each have a protrusion region, which enables the holding device to be secured against rotation in a particularly simple and effective manner.

In a further advantageous further development of the invention, at least one haptic element of the at least two haptic elements is elastically deformable when the contact pressure force is exerted. This is advantageous because the at least two haptic elements can thus be pretensioned in order to exert the contact pressure on the wall area. Due to the elastic deformation of the haptic elements, a permanent exertion of the contact pressure by the haptic elements is rendered possible, whereby the holding device can be fixed in the interior of the eye in a correspondingly permanently stable manner.

In a further advantageous further development of the invention, at least one haptic element of the at least two haptic elements is formed in an arcuate shape. This is advantageous because an arcuate design not only enables particularly simple elastic deformability, but also enables gentle cushioning of the tissue, for example of impact loads or vibrations. As a result of the exertion of the contact pressure force, a radius of curvature of the arcuately shaped haptic element can be reduced, whereby a particularly uniform flow of force can be achieved without any stress peaks in the haptic element.

In a further advantageous further development of the invention, the holding device comprises at least one receiving component which is connected to the at least two haptic elements and to which the optical implant can be reversibly detachably fixed. This is advantageous because the optical implant can be replaced particularly easily in a non-destructive manner if necessary, without having to replace the holding device for this purpose. The holding device can thus remain permanently in the interior of the eye so that a simple exchange of the optical implant is facilitated by a particularly gentle, minimally invasive procedure. The receiving component can preferably have a holding frame in which the optical implant can be fixed in a particularly stationary and secure manner.

In a further advantageous further development of the invention, at least one haptic element of the at least two haptic elements is connected to the at least one receiving component at a first end region of the at least one haptic element, and the at least one protrusion region is arranged at a second end region opposite the first end region. This is advantageous because the at least one haptic element thus has a particularly high functionality. On the one hand, the at least one haptic element thus serves to hold the receiving component and, on the other hand, to provide support on the wall area. Due to this high functionality of the at least one haptic element, a particularly simple and compact design of the holding device as well as its low-effort fixation in the eye interior without suture fixation is rendered possible.

In a further advantageous further development of the invention, opposite end regions of at least one haptic element of the at least two haptic elements are connected to the receiving component and at least one central region of the at least one haptic element arranged between the respective end regions is spaced apart from the receiving component, the at least one protrusion region being arranged on the at least one central region. This is advantageous, since a particularly stable fixation between the haptic element and the receiving component is formed by the connection of the at least one haptic element at its mutually opposite end regions. The fact that the protrusion region is arranged on the central region arranged between the end regions enables a particularly uniform load distribution of the contact pressure, or of a force resulting from the contact pressure, over the end regions, as a result of which, for example, stresses or torsions within the receiving component can be kept low.

In a further advantageous further development of the invention, the at least one receiving component is elastically deformable by the at least two haptic elements when the contact pressure is exerted. This is advantageous because the receiving component thus has a dual function. Thus, the receiving component is not only used for reversibly releasable fixation of the optical implant, but also contributes to exerting the contact pressure.

In a further advantageous further development of the invention, the at least one receiving component is designed to expand, while exerting the contact pressure, at least in some areas from a non-use shape, in which the holding device can be inserted at least in some areas through the eye interior bounded by the wall area, into a receiving shape, in which the optical implant can be fixed to the at least one receiving component. This is advantageous because the receiving component can thus have a smaller dimension in at least one direction of extension, for example in a transverse direction of extension, in the non-use shape than in the receiving shape. Because of the smaller dimension in the non-use shape, easier insertion of the holding device into the interior of the eye is rendered possible. Due to the fact that the retaining component in its receiving shape compared to the non-use shape is expanded means that the optical implant can be held on the retaining component (in its receiving shape) in a particularly loss-proof manner. The possibility of expanding from the non-use shape into the receiving shape makes the holding device particularly suitable for micro-incisions.

In a further advantageous further development of the invention, the at least one receiving component comprises at least one clamping region to which the optical implant can be clamped and thereby releasably fixed. This is advantageous because the clamping area allows the optical implant to be clamped in place and thus enables the optical implant to be fixed to the receiving component in a particularly simple reversibly releasable manner.

In a further advantageous further development of the invention, the holding device is formed in one piece. This is advantageous because it allows the holding device to be handled with particularly little effort when fixing it in the interior of the eye.

A second aspect of the invention relates to an optical device with a holding device according to the first aspect of the invention and with an optical implant held on the holding device. Such an optical device can be fixed in an interior of an eye with particularly low effort. The features presented in connection with the holding device according to the first aspect of the invention as well as the advantages thereof apply accordingly to the optical device according to the second aspect of the invention and vice versa.

The optical implant may be generally foldable to facilitate insertion of the optical implant into the interior of the eye. After insertion into the interior of the eye, the optical implant may be unfolded to fix the optical implant in the interior of the eye.

In a further advantageous further development of the invention, the optical device is formed in one piece. This is advantageous because it allows the optical device to be handled with particularly little effort when it is fixed in the interior of the eye.

In a further advantageous further development of the invention, the optical implant is reversibly detachably fixed to the holding device. This is advantageous because the optical implant can be replaced particularly easily without having to destroy the holding device. The holding device in this process can remain in the interior of the eye so that a particularly small opening or a particularly small incision in the eye is sufficient to replace the optical implant.

The features and combinations of features mentioned above in the description, as well as the features and combinations of features mentioned below in the description of the figures and/or shown alone in the figures can be used not only in the combination indicated in each case but also in other combinations or on their own without departing from the scope of the invention.

BRIEF DESCRIPTION OF THE DRAWING FIGURES

Further advantages, features, and details of the invention will be apparent from the claims, the following description of preferred embodiments, and from the drawings.

In the following, the invention is explained once again with reference to a specific example of an embodiment. For this purpose shows:

FIGS. 1a-b show schematic sectional views of a partial region of an eye and respective top views of an optical device which can be supported on a wall area of the eye bounding the interior of the eye, the optical device being detached from the wall area in FIG. 1a and supported on the wall area in FIG. 1b;

FIGS. 2a-b show in each case further schematic sectional views of the partial region of the eye and respective top views of a holding device for holding an optical implant, the holding device being detached from the wall area in FIG. 2a and supported on the wall area in FIG. 2b;

FIGS. 3a-b show respective further schematic sectional views of the partial eye region and respective top views of a variant of the holding device for holding the optical implant, the holding device being detached from the wall area in FIG. 3a and supported on the wall area in FIG. 3b;

Figure 4B:
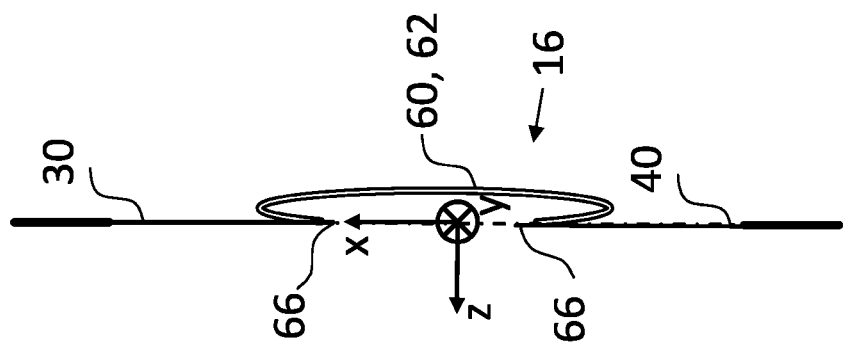
FIG. 4b shows a schematic side view of the variant of the holding device shown in FIG. 4a in its non-use shape.
Figure 4A:
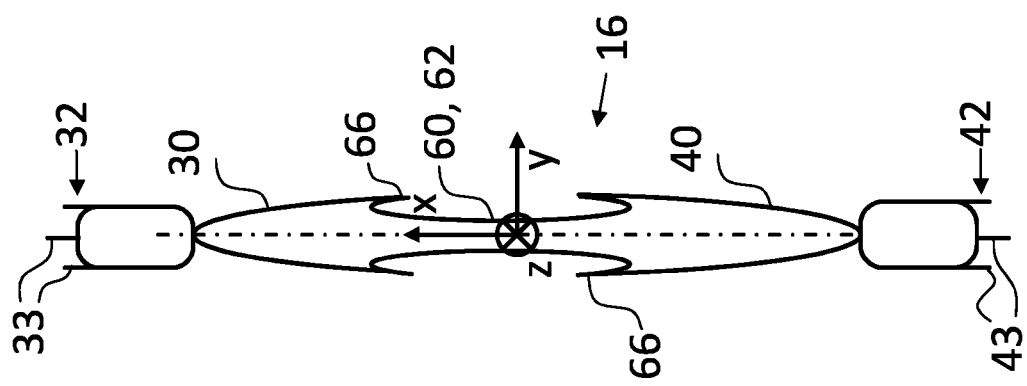
FIG. 4a shows a schematic top view of a further variant of the holding device for holding the optical implant, the holding device being shown in a non-use shape.
Figure 4C:
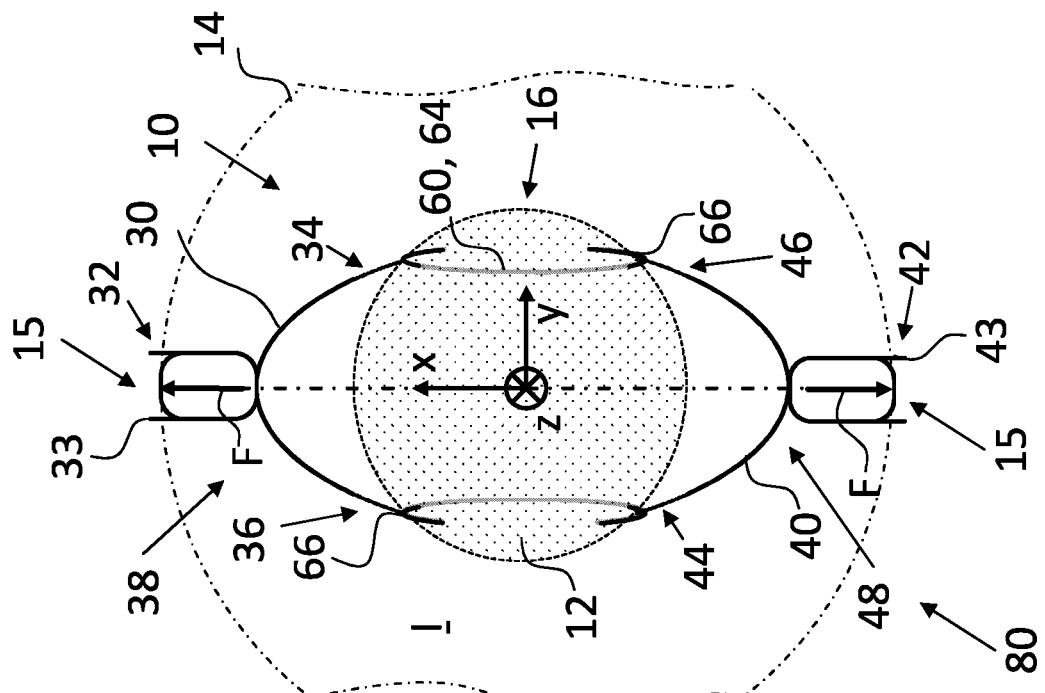
Figure 4D:
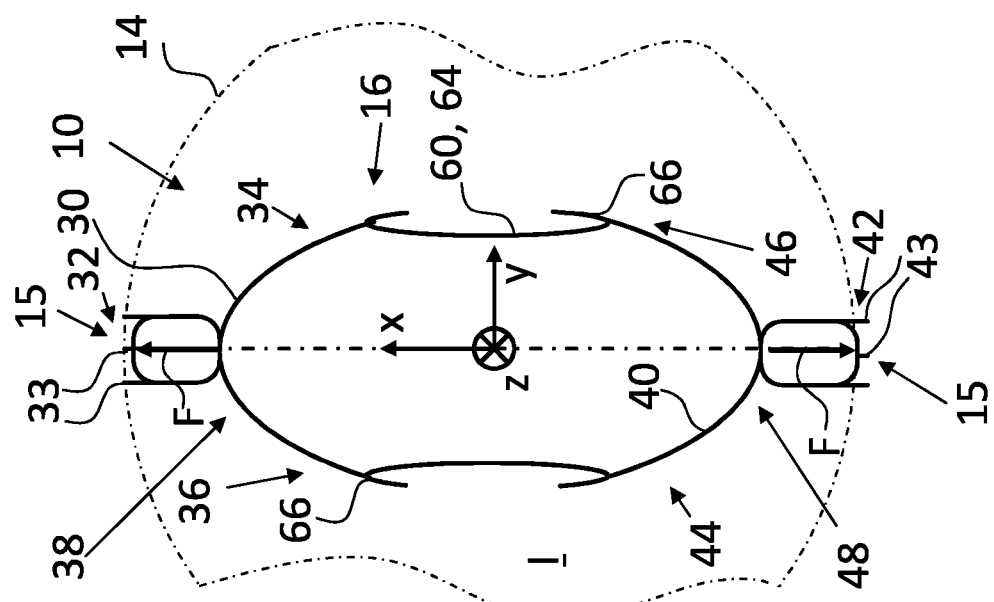

FIG. 4c shows a schematic top view of the further variant of the holding device for holding the optical implant, wherein the holding device is shown in a receiving shape in which the holding device is expanded compared to the non-use shape and is supported on the wall area; and FIG. 4d shows a schematic top view of the further variant of the holding device in its receiving shape, wherein the optical implant is reversibly releasably fixed to the holding device.

DESCRIPTION OF THE INVENTION

FIG. 1a and FIG. 1b each show an optical device 80, which comprises a holding device 10 and an optical implant 12 held on the holding device 10. The optical implant 12 in the present case is designed as an intraocular lens.

The optical device 80 may be generally of one-piece construction. Alternatively, the optical implant 12 may be reversibly releasably fixed to the holding device 10 so that the holding device 10 may be provided or fixed in an eye interior I of an eye independently of the optical implant 12, as can be seen from FIG. 2a to FIG. 4c. The holding device 10 may be generally formed in one piece.

In FIG. 1a to FIG. 4c, coordinate systems related to the optical device 80 and to the holding device 10, respectively, are indicated, which are defined by a longitudinal extension direction x, by a transverse extension direction y, and by a vertical extension direction z of the optical device 80 and the holding device 10, respectively.

FIG. 2a to FIG. 4c respectively show the holding device 10 for holding the optical implant 12 on a wall area 14 of the eye in the eye interior I. The holding device 10 generally comprises a retaining component 16 by which a contact pressure force F can be exerted on the wall area 14 and thereby the retaining component 16 can be supported on the wall area 14. The contact pressure force F is generally exerted on the wall area 14 using the retaining component 16 when the retaining component 16 is in a braced state (relative to the wall area 14), i.e. as soon as the holding device 10 is inserted into the eye interior I and the retaining component 16 is in supporting abutment with the wall area 14, as can be seen in FIG. 1b, FIG. 2b, FIG. 3b, FIG. 4c, and FIG. 4d.

In FIG. 1a, FIG. 2a, FIG. 3a, FIG. 4a, and FIG. 4b the retaining component 16 is shown in a relaxed state outside the eye interior I, whereby at least in FIG. 1a, FIG. 2a, and FIG. 3a, in which the holding device 10 and the optical device 80, respectively, are not yet inserted into the interior of the eye I, it can be seen that the retaining component 16 in the relaxed state has a greater extension, at least in the longitudinal direction of extension x, than the wall area 14. In the relaxed state, the retaining component 16 thereby projects beyond an inner diameter of the wall area 14 in the longitudinal direction of extension x. Accordingly, two haptic elements 30, 40 of the retaining component 16 in its relaxed state project beyond the wall area 14 in the longitudinal extension direction x, as can be seen at least in FIG. 1a, FIG. 2a, and FIG. 3a.

The retaining component 16 is generally designed to penetrate, at least in certain areas, into a wall area tissue 15 of the wall area 14 when the contact pressure force F is exerted, and additionally or alternatively to exert pressure on the wall area 14 at specific points. For this purpose, the retaining component 60 has respective protrusion regions 32, 42, from each of which a plurality of protrusion elements 33, 43 extend away, as can be seen from the synopsis of FIG. 1a to FIG. 4c. The protrusion elements 33 are generally associated with and disposed on the protrusion region 32. The protrusion elements 43 are generally associated with and arranged on the protrusion region 42. The protrusion elements 33, 43 are formed as respective tips.

At least some of the protrusion elements 33, 43 may also be formed as respective strut elements, but this is not further illustrated herein. The strut elements may have a triangular cross-section in a plane perpendicular to their main extension direction. This plane can be defined by the longitudinal direction of extension x and by the transverse direction of extension y.

The protrusion regions 32, 42 are presently arranged on the haptic elements 30, 40, by which the contact pressure F can be exerted on the wall area 14 and which each have one of the protrusion regions 32, 42. The protrusion region 32 is assigned to the haptic element 30, whereas the protrusion region 42 is assigned to the haptic element 40.

The haptic elements 30, 40 are generally elastically deformable under the exertion of the contact pressure F and are configured to be arcuate in shape.

The holding device 10 may generally comprise a receiving component 60 which is connected to the haptic elements 30, 40 and to which the optical implant 12 is reversibly releasably fixable, as can be seen in particular in FIG. 2a to FIG. 4d.

The haptic elements 30, 40 may be connected to the receiving component 60 at a respective first end region 34, 44 and the respective protrusion regions 32, 42 may be arranged at a respective second end region 36, 46 opposite the first end region 34, 44, as can be seen, for example, in FIG. 1a, FIG. 1b, FIG. 2a, FIG. 2b. The first end region 34 and the second end region 36 are associated with the first haptic element 30, whereas the first end region 44 and the second end region 46 are associated with the second haptic element 40.

FIG. 3a to FIG. 4d show that the opposite end regions 34, 36, of the first haptic element 30 and the opposite end regions 44, 46 of the second haptic element 40 can also be connected to the receiving component 60. As a result, the haptic elements 30, 40 are each connected to the receiving component 60 on both sides, so to speak, whereby the haptic elements 30, 40 do not have any free ends. A central region 38 of the first haptic element 30 arranged between the respective end regions 34, 36 and a central region 48 arranged between the respective end regions 44, 46 of the second haptic element 40 can thereby be spaced apart from the receiving component 60. The respective central regions 38, 48 extend away from the receiving component 60 in the longitudinal extension direction x in the present case. The protrusion region 32 may be arranged at the central region 38, whereas the protrusion region 42 may be arranged at the central region 48. In other words, the protrusion region 32 may be associated with the central region 38 of the first haptic element 30 and the protrusion region 42 may be associated with the central region 48 of the second haptic element 40.

From the synopsis of FIG. 4a to FIG. 4d, it can be seen that the receiving component 60 may be deformable by the haptic elements 30, 40 when the contact pressure F is exerted. The receiving component 60 may be designed to expand, under the exertion of the contact pressure F, at least in certain areas from a non-use shape 62 shown in FIG. 4a and FIG. 4b, in which the holding device 10 can be inserted particularly easily into the eye interior I bounded at least in certain areas by the wall area 14, into a receiving shape 64 shown in FIG. 4c and FIG. 4d, in which the optical implant 12 can be fixed reversibly releasably to the at least one receiving component 60. Particularly from the synopsis of FIG. 4a with FIG. 4c, it can be seen that a corresponding expanding of the receiving component 60 can take place when it is deformed from the non-use shape 62 into the receiving shape 64 in the transverse direction of extension y. In this case, insertion of the holding device 10 into the eye interior I in the longitudinal extension direction x can take place through a particularly small opening in the wall area 14, which is not shown further here, especially since the receiving component 60 in the non-use shape 62, which is particularly clearly recognizable in FIG. 4a, has a smaller extension in the transverse extension direction y, i.e. is narrower in the present case than in the receiving shape 64, which is particularly clearly recognizable in FIG. 4c.

FIG. 2a to FIG. 4d show that the receiving component 60, which can be generally formed as a frame or as a frame element, can comprise a plurality of clamping areas 66 to which the optical implant 12 can be clamped and thereby releasably fixed. The clamping regions 66 may be configured as respective retaining hooks to which the optical implant 12 may be clamped. For this purpose, the clamping areas 66 can each embrace the optical implant 12 at least in some areas.

In order to enable a particularly simple, low-effort and, above all, statically determined mounting of the optical implant 12 on the receiving component 60, the receiving component 60 can comprise exactly three clamping regions 66, although four clamping regions 66 are shown in the present case. The exactly three clamping regions 66 can be arranged regularly in a plane spanned by the longitudinal direction of extension x and the transverse direction of extension y, or in a plane parallel thereto. The clamping areas 66 can have an angular distance of 120° from each other, which enables a particularly precise alignment of the optical implant 12 when it is fixed by the clamping areas 66.

Generally, a self-fixing system for holding the optical implant 12 is provided by the holding device 10. The optical implant 12 can generally be formed as a lens, in particular as an intraocular lens. The holding device 10 is designed to be supported on the wall portion 14 while exerting the contact pressure F, and is thereby secured against rotational movements within the interior of the eye I. The holding device 10 can fix itself with the respective protrusion elements 33, 43 in the wall area 14 and thereby, for example, claw itself in the wall area 14, whereby a particularly durable fixation is provided.

In their respective relaxed state, i.e. before their insertion into the interior of the eye I or before their fixation to the wall area 14, the holding device 10 or the optical device 80 have a greater extension in at least one extension direction, for example in the longitudinal direction x, than the wall area 14, which can be, for example, a capsular bag or a sulcus (sulcus sclerae) of the eye. This allows the holding device 10 or the optical device 80 to be braced with respect to the wall area 14, thereby allowing the contact pressure force F to be exerted on the wall area 14. The holding device 10 enables the optical implant 12 provided by a surgeon to be held in a position-secured manner in the interior of the eye I and supported against the wall area 14.

Both the holding device and the optical device 80 can be inserted in a respective, folded state into the eye and thus into the interior of the eye I by an injector without having to make a large opening in the form of a cut on the wall area 14 for this purpose.

The invention claimed is:

1. A holding device for holding an optical implant on a wall area in an eye interior of an eye, comprising at least one retaining component, by which a contact pressure can be exerted on the wall area and, as a result thereof, thereby the at least one retaining component is supported at the wall area, wherein said at least one retaining component has at least one protrusion region, from which at least one protrusion element extends away, which is configured and arranged to, when the contact pressure force is exerted, penetrate at least regionally into a wall area tissue of the wall area and/or to exert punctiform pressure on the wall area;

wherein said at least one retaining component comprises at least two haptic elements by which the contact pressure can be exerted on the wall area, wherein the at least one protrusion region is arranged on at least one haptic element of the at least two haptic elements;

wherein the holding device comprises at least one receiving component which is connected to the at least two haptic elements and to which the optical implant can be reversibly releasably fixed; and wherein said at least one receiving component is configured and arranged to expand, under the exertion of the contact pressure, at least regionally from a non-use shape, in which the holding device is introduced into the eye interior bounded at least regionally by the wall area, into a receiving shape, in which the optical implant is fixed reversibly detachably to the at least one receiving component.

2. The holding device according to claim 1, wherein at least one haptic element of the at least two haptic elements is elastically deformable under the exertion of the contact pressure.

3. The holding device according to claim 1, wherein at least one haptic element of the at least two haptic elements is configured to be arcuate.

4. The holding device according to claim 1, wherein at least one haptic element of the at least two haptic elements is connected to the at least one receiving component at a first end region of the at least one haptic element, and the at least one protrusion region is arranged at a second end region opposite the first end region.

5. The holding device according to claim 1, wherein opposite end regions of at least one haptic element of the at least two haptic elements are connected to the receiving component, and at least one central region of the at least one haptic element arranged between the respective end regions is spaced apart from the receiving component, the at least one protrusion region being arranged on the at least one central region.

6. The holding device according to claim 1, wherein the at least one receiving component is elastically deformable under the exertion of the contact pressure by the at least two haptic elements.

7. The holding device according to claim 1, wherein the at least one receiving component comprises at least one clamping region to which the optical implant is fixed reversibly detachably.

8. The holding device according to claim 1, wherein the holding device is formed in one piece.

9. An optical device comprising a holding device according to claim 1 and an optical implant held on the holding device.

10. The optical device according to claim 9, wherein the optical device is formed in one piece.

11. The optical device according to claim 9, wherein the optical implant is reversibly detachably fixed to the holding device.

\* \* \* \* \*